United States Patent
Wietholt

[19]

[11] Patent Number: 6,134,469
[45] Date of Patent: Oct. 17, 2000

[54] IMPLANTABLE HEART STIMULATOR

[76] Inventor: Dietmar Wietholt, Mollmannsweg 18e, D-48161 Munster, Germany

[21] Appl. No.: 09/171,280
[22] PCT Filed: Apr. 19, 1997
[86] PCT No.: PCT/EP97/01989
  § 371 Date: Jul. 6, 1999
  § 102(e) Date: Jul. 6, 1999
[87] PCT Pub. No.: WO97/39798
  PCT Pub. Date: Oct. 30, 1997
[51] Int. Cl.[7] ..................................................... A61N 1/362
[52] U.S. Cl. .................................................................. 607/14
[58] Field of Search .................................. 607/5, 4, 9, 14

[56] References Cited

U.S. PATENT DOCUMENTS 4,467,810  8/1984  Vollmann .
5,312,451  5/1994  Limousin et al. .

FOREIGN PATENT DOCUMENTS

0488840A1  11/1991  European Pat. Off. .
0550342A1  12/1992  European Pat. Off. .
221372 A1  4/1985  Germany .

*Primary Examiner*—Scott M. Getzow
*Attorney, Agent, or Firm*—Fulbright & Jaworski, LLP

[57] ABSTRACT

An implantable cardioverter-defibrillator and/or heart pacemaker has a programmable electrical circuit for producing series of stimulation impulses, wherein electrical circuit is able, on detection of one or more successive extrasystole(s) not observing the natural frequency fe, to produce a series of stimulation impulses (SI) of a higher frequency fs(t) in relation to the earlier natural frequency. The higher frequency (shorter interval) is programmable between 50% and 100% of the mean interval between two or more natural systoles. The interval is dependent on the prematurity of the extrasystole. The frequency than subsequently falls steadily below the natural frequency or ends with the natural frequency fe. There is an immediately decrease—linear or exponential—in frequency and no acceleration due to multiple extrasystoles in order to avoid a continuous higher heart rate.

8 Claims, 1 Drawing Sheet

IMPLANTABLE HEART STIMULATOR

BACKGROUND AND SUMMARY OF THE INVENTION

The invention relates to an implantable cardioverter-defibrillator and/or cardiac pacemaker for stimulating the cardiac muscle (cardiac stimulation device), with at least one electrode for connection to the heart muscle, a programmable electrical circuit for producing series of stimulation impulses with impinge upon the electrode, and with an electronic memory connected to said circuit, with which over several periods of the heart beat the electrical phenomena inherent in the heart-beat, in particular systoles and their characteristic frequency $f_c$, can be recorded and stored, the electrical circuit evaluating the stored electrical phenomena and emitting corresponding series of anti-tachycardiac and anti-bradycardiac stimulation impulses.

The two most important types of cardiac stimulation devices, cardioverter-defibrillators and so-called pacemakers, conventionally operate using types of stimulation which begin after the onset of cardiac tachyarrhythmias.

Cardiac stimulation devices of this type, in the form of cardioverter-defibrillators and or pacemakers with anti-tachycardiac or anti-bradycardiac modes of stimulation are known, for example according to U.S. Pat. No. 4,052,991 and U.S. Pat. No. 3,857,399. However, the stimulation devices according to the state of art emit stimulation impulses which, during anti-tachycardiac function, begin with a 1-s time delay after the onset of the tachycardia.

They operate in correspondence, that is, the period duration of the stimulation impulses is shorter than the duration of the systoles in tachycardia. This shortened impulses series is intended to "intercept" the extrasystoles, which become present in tachycardia. On perception of the systole frequencies arising during tachycardia, the delay time is followed by a continuous stimulation at a frequency $f_s$, which is higher than the characteristic frequency, $f_e$. This frequency $f_s$ is for the most part held constant.

The aim is to provide a cardiac-stimulation device, which is capable of preventing the occurrence of tachycardia at an early stage.

The aim is achieved by a cardiac-stimulation device, namely a cardioverter-defibrillator or a pacemaker of the type named in the preamble, characterized in that the electrical circuit is able, on detection of one or more of successive extrasystole(s) not of the characteristic frequency $f_e$, to produce a series of stimulation impulses of frequency $f_g(t)$ which, after the appearance of extrasystole(s), begin after a programmable time interval (between 50 and 100% of $t_{mean}$) at a frequency $f_{gi}$ higher than the detected previous frequency $f_g$ and are then steadily retarded, i.e. they steadily decrease in frequency $f_g$ until the frequency $f_g(t)$ essentially corresponds to the characteristic frequency $f_e$, in particular that the frequency $f_g(t)$ falls below the characteristic frequency $f_g$ to a frequency $f_{sub}$ or ends with the frequency $f_c$.

This type of production of a series of stimulation impulses is embodied in a cardiac stimulation device, which is itself known, as characterized in generic term in claim 1.

Following an extrasystole, the cardiac-stimulation device according to the invention produces an initially more rapid series of stimulation impulses at a higher frequency $f_{gi}$ than frequency $f_c$ (characteristic or natural frequency). A steady slowing then follows, until the frequency $f^*(t)$ corresponds to the characteristic frequency $f_c$. The frequency $f_g$ preferably ends on attaining the characteristic frequency $f_c$.

The cardiac-stimulation device according to the invention is therefore capable of producing, in addition to the known and still available modes of stimulation, another mode of stimulation setting in after each extrasystole, which is followed by a longer "compensatory" pause, without a prior delay of the order of 1 s for the first stimulation impulse, as in the state of art. It is therefore proposed that the time interval $t_i$ between the extrasystole and the first stimulation impulse is programmable with the frequency $f_{gi}$. The time interval $t_i$ between the extrasystole and the first stimulation impulse preferably being, for example, between 60 and 90% of a mean time interval $t_{mean}$ between two systoles of characteristic frequency. The percentage can be variably programmed according to the prematurity of the extrasystole.

The frequency retardation may, for example, be such that the time between the stimulation impulses increases by at least 3% from one impulse to another, preferably by 6–18%.

To determine the frequency, a mean time interval $t_{mean}$ between two systoles of characteristic frequency is determined as a floating mean value over a plurality, for example 2–5, heartbeat periods.

On occurrence of two extrasystoles (ES) at a differing time interval, the frequency determination begins at the last systole corresponding to the characteristic frequency.

Retardation of the initially higher frequency may be linear, for example according to the equation:

$$f_g(t) = f_{gi}(1 + t \cdot (f_e - f_{si})/t_2)$$

where $t_2$ is the endpoint of stimulation, when $f_{gi}$ is equal to $f_e$ or – in case of a missing characteristic frequency—the anti-bradycardiac rate of the pacemaker.

Retardation of the initially higher frequency may also be exponential, for example according to the equation:

$$f_g(t) = f_{si} \cdot e^{alpha \cdot t}$$

where alpha=$(1/t_2) \cdot \ln(f_e/f_{gi})$

Another useful property of the cardiac-stimulation device is that, on detection of a further extrasystole, the stimulation sequence currently operating can be discontinued and restarted after the extrasystole. This also ensures that characteristic normal systoles of the heart are not counterstimulated.

The aforesaid cardiac-stimulation device is further characterized in that it can be used to stimulate within the atrium and/or the ventricle of the heart.

BRIEF DESCRIPTION OF THE FIGURES

An embodiment of the invention is illustrated by means of two schematic cardiograms. The figures show.

DETAILED DESCRIPTION

Figure 1:
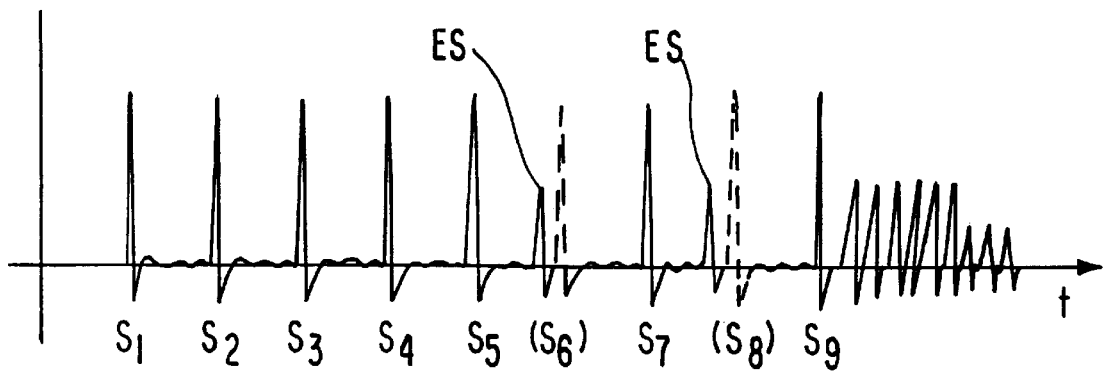
FIG. 1 An electrocardiogram of untreated tachycardia with preceding extrasytoles.

FIG. 1 shows in schematic form with the time t along the x-axis the occurrence of systoles $S_1$, $S_2$, $S_3$, $S_4$ and $S_5$ at a normal interval of characteristic frequency. The dotted line represents the point in time at which another 'normal' systole, $S_6$, of characteristic frequency is anticipated. In this case, however, an extrasystole ES occurs. Here the interval between $S_5$ and ES is shorter than the normal distance between two systoles.

At the anticipated time based on the characteristic frequency $f_e$, another systole $S_7$ occurs; again this is followed by an extrasystole ES at a shorter time interval from the systole that one would have anticipated at a normal frequency (characteristic frequency) been maintained. However, there is no anticipated normal systole S*. There arises the so-called compensatory pause before the occurrence of a further systole S*, which in many cases is followed by a so-called tachycardia (increase in heart rate to over 100 beats per minute). Such a tachycardia is of "worse prognosis" (see *PRCHYREMBEL*, Klinisches Woerterbuch, 255$^{th}$ Aufl. Chap. "Tachykardic").

Figure 2:
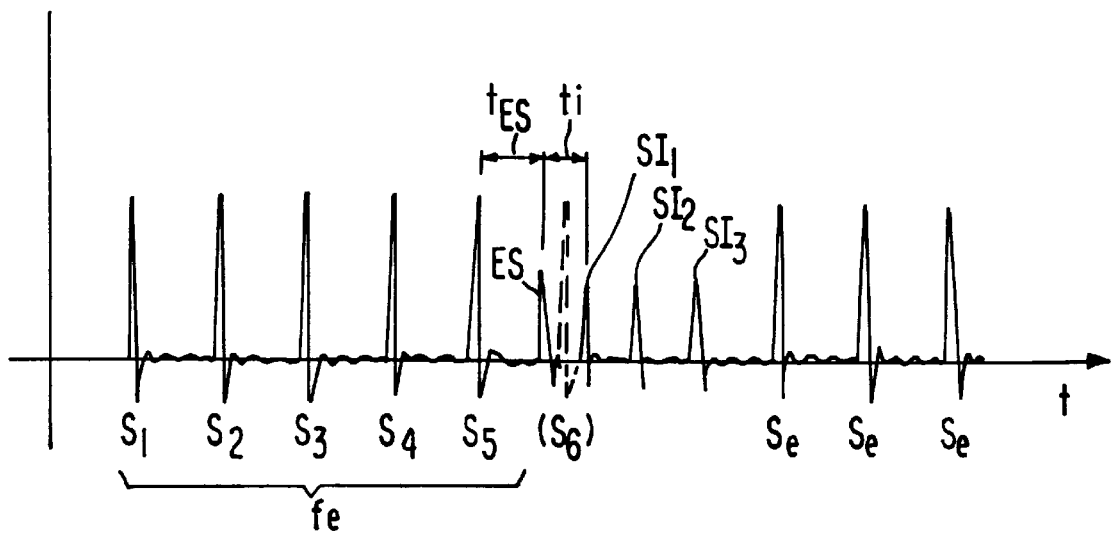
FIG. 2 A stimulation sequence on occurrence of extrasystoles for the prophylaxis of tachycardia.

FIG. 2 shows the same initial situation. The systoles of normal frequency $f_e$, $S_1$–$S_5$ arise at equal and normal time intervals. An extrasystole ES then arises at a shorter interval than corresponds to the frequency $f_e$. The systole $S_6$ (dotted) is absent. During the ensuing compensatory pause after occurrence of the extrasystole ES, the cardiac-stimulation device according to the invention triggers a stimulation impulse $SI_1$ in the atrium and/or the ventricle of the heart at a shorter or equal time interval (50–100%) than the interval between the two normal systoles $S_1$, $S_2$ . . . $S_5$; said stimulation impulse $SI_1$ being followed by a second and a third stimulation impulse $I_2$ and $SI_3$.

Depending on the delay of the ES, i.e. between 200 and 600 milliseconds (ms), a variation of $t_i$ between 50 and 100% of the mean time interval $t_{mean}$ is possible following in correspondence to this table:

| prematurity of ES | $t_1$ in % of $t_{mean}$ |
|---|---|
| ≦200 ms | 60 |
| ≦300 ms | 70 |
| ≦400 ms | 80 |
| ≦500 ms | 90 |
| ≦600 ms | 100 |

In FIG. 2 the intervals between stimulation impulses are each drawn at 10% greater than the preceding one. In reality, the increase in only 3–5%. Stimulation impulses are emitted until a normal characteristic systole $S_e$ has been reoccurred. Stimulation impulses will be emitted until a characteristic systole reoccurs.

Once a new extrasystole arise a new series of stimulation impulses $SI_1$, $SI_2$ . . . is triggered. In this case the currently operating stimulation impulse sequence is discontinued and restarted after occurrence of the extrasystole.

It is demonstrated that tachycardia can evidently be prevented in many cases by the impulse sequences produced by the cardiac-stimulation deevice.

What is claimed is:

1. An implantable cardiac-stimulation device, comprising at least one electrode for connection to heart muscle;
   a programmable electrical circuit for producing series of stimulation impulses which impinge upon the electrode; and
   an electronic memory connected to said electrical circuit, with which over several periods of the heart beat the electrical phenomena inherent in the heart-beat, systoles and their characteristic frequency fe, are recorded and stored;
   the electrical circuit evaluating the stored electrical phenomena and emitting corresponding series anti-tachycardiac and anti-bradycardiac stimulation impulses, wherein the electrical circuit is able, on detection of one or more successive extrasystoles not of the characteristic frequency fe, to produce a series of stimulation impulses (SI) of frequency fs(t) which, after the appearance of extrasystole(s), after programmable time interval ti between 50% and 100% of tmean between two characteristic systoles, begin at a higher frequency fsi and than steadily retarded, such that these is a steady decrease in frequency until the frequency fs(t) falls below the characteristic frequency or essentially corresponds to the characteristic frequency fe.

2. The cardiac-stimulation device according to claim 1 wherein the time interval ti between the extrasystole (ES) or the last of more than one extrasystoles and the first stimulation impulse (1$^{st}$ SI) is programmable between 60 and 90% of the mean time interval tmean between two systoles of characteristic frequency.

3. The cardiac-stimulation device according to claim 1 wherein the time interval ti is variable corresponding to the time period tes between the occurrence of an extrasystole (ES) and the last normal systole (Se).

4. Cardiac-stimulation device according to claim 1 wherein the mean time interval tmean between two systoles of characteristic frequency is determined as the floating mean value over more than one heartbeat periods.

5. The cardiac-stimulation device according to claim 1 wherein retardation of the initially higher frequency fsi is linear according to the equation:

$$fs(t)=fsi(1+t\cdot(fe-fsi)/t2)$$

wherein t2 is the endpoint of the stimulation series, with fs=fe or – in case of a missing characteristic frequency—the bradycardiac stimulation rate of the pacemaker.

6. The cardiac-stimulation device according to claim 1 wherein retardation of the initially higher frequency fsi is exponential, i.e. according to the equation:

$$fs(t)=fsi\cdot e^{alpha \cdot t}$$

wherein alpha=$(1/t_2)\cdot \ln(fe/fsi)$.

7. The cardiac-stimulation device according to claim 1 wherein if another extrasystole occurs, the currently operating stimulation impulse sequence is discontinued and restarted after the extrasystole.

8. The cardiac-stimulation device according to claim 1, wherein ti can be used to stimulate within the atrium and/or the ventricle of the heart.

* * * * *